United States Patent [19]

Iwata et al.

[11] 4,414,073
[45] Nov. 8, 1983

[54] SUPPORTING BODY CELL IN ELECTROPHORETIC APPARATUS

[75] Inventors: Toyotaro Iwata, Kobe; Kunio Nakajima, Miki; Hiroyuki Otsuki, Kakogawa, all of Japan

[73] Assignee: Toa Medical Electronic Co., Ltd., Hyogo, Japan

[21] Appl. No.: 419,034

[22] Filed: Sep. 16, 1982

[30] Foreign Application Priority Data

Sep. 18, 1981 [JP] Japan ............................ 56-147164

[51] Int. Cl.³ .......................................... G01N 27/28
[52] U.S. Cl. ............................ 204/299 R; 204/180 G
[58] Field of Search ............ 204/299 R, 180 G, 180 R

[56] References Cited

U.S. PATENT DOCUMENTS

| | | | |
|---|---|---|---|
| 3,715,295 | 2/1973 | Tocci | 204/180 G |
| 3,873,433 | 3/1975 | Seidel et al. | 204/180 G |
| 3,951,776 | 4/1976 | Eibl et al. | 204/299 R |
| 4,194,963 | 3/1980 | Denckla | 204/299 R |

Primary Examiner—Howard S. Williams
Assistant Examiner—Terryence F. Chapman
Attorney, Agent, or Firm—Pearne, Gordon, Sessions, McCoy, Granger & Tilberry

[57] ABSTRACT

The leg of a tray constituting an electrophoretic cell and accommodating a gel layer are provided with a centrally located partitioning member to eliminate uneven current density over the entire gel layer when the cell is energized during electrophoresis.

10 Claims, 7 Drawing Figures

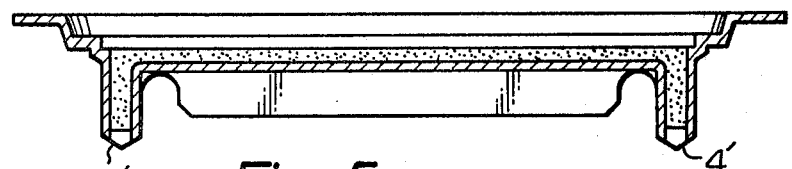
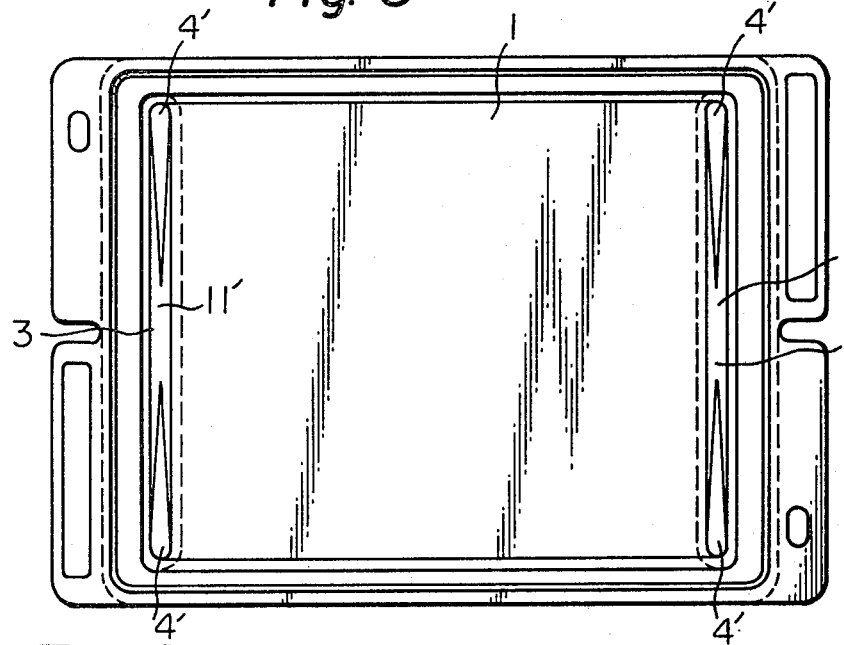
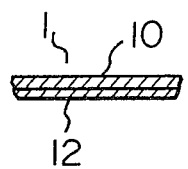
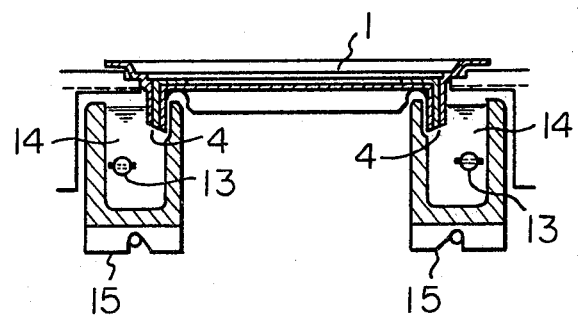

SUPPORTING BODY CELL IN ELECTROPHORETIC APPARATUS

BACKGROUND OF THE INVENTION

This invention relates to a cell for accommodating a supporting body such as agarose gel for the electrophoretic separation and measurement of albumin contained in body fluids and, more particularly, to a cell suited for use in an automated analyzing apparatus for achieving highly accurate measurements.

In order to electrophoretically isolate various kinds of albumin contained in body fluids, it is conventional practice to form a layer of a supporting body, namely a gel made of agar-agar, agarose or the like, to a predetermined thickness on a plastic film or glass plate, provide holes in the gel layer at predetermined positions for the application of samples of blood serum or the like, introduce the samples into the holes, dispose the film or plate in an electrophoretic compartment, form a bridge, made of a buffer solution-permeated sponge or the like, from both ends of the gel into buffer tanks filled with a buffer solution and accommodating electrodes, and carry out electrophoresis by introducing an electric current from the buffer tanks into the gel via the bridges.

An electrophoretic method which has come into use in recent years teaches to form the gel layer on a plastic film, bend both the film and the gel layer simultaneously during electrophoresis to immerse both ends thereof directly into the buffer solution contained in the buffer tanks accommodating the electrodes, and then passing an electric current through the gel.

In an apparatus adapted to automatically apply samples to the sample holes and to automatically read the separated substances, however, the foregoing methods of forming bridges by means such as sponges or of bending the gel layer entail considerable human labor and cannot be applied to the automated apparatus.

SUMMARY OF THE INVENTION

Accordingly, an object of the present invention is to provide a cell for a supporting body, which cell can be handled by an automated analyzing and measuring apparatus in a very simple and reliable manner.

Another object of the present invention is to provide a cell for a supporting body, which cell can be used in performing highly accurate electrophoretic measurements even in an electrophoretic apparatus that operates on the basis of conventional electrophoretic techniques.

A further object of the present invention is to provide a cell for a supporting body, wherein a uniform temperature and current density are maintained at all times to enable correct isolation of sample components and accurate quantitative determinations in electrophoresis.

According to the present invention, these and other objects are attained by providing a cell for a supporting body in an electrophoretic apparatus, including a tray having a recessed floor, a pair of laterally extending legs each located on two opposing sides of the tray, each leg having apertures extending from the lower end thereof and opening into the floor of the tray to communicate with the recessed portion thereof, and partitioning members located between adjacent ones of the apertures. A gel layer is formed on the floor to a uniform thickness measured from the floor, with the gel filling the apertures in the legs down to the lower end face of the legs. The apertures and partitioning members are so dimensioned as to provide a uniform temperature distribution and current density across the cell during electrophoresis, whereby the resulting fractionated pattern of a sample gives a truer indication of the components contained in the sample.

Other features and advantages of the invention will be apparent from the following description taken in conjunction with the accompanying drawings in which like reference characters designate the same or similar parts through the figures thereof.

BRIEF DESCRIPTION OF THE DRAWINGS

FIG. 4 is a side section illustrating a third embodiment of a supporting cell according to the present invention;

FIG. 5 is a plan view illustrating a fourth embodiment of a supporting cell according to the present invention;

FIG. 6 is a fragmentary side section illustrating a fifth embodiment of a supporting cell according to the present invention; and FIG. 7 is a side section useful in describing electrophoresis conducted using a supporting cell embodying the present invention.

DETAILED DESCRIPTION OF THE PREFERRED EMBODIMENT

Figure 1:
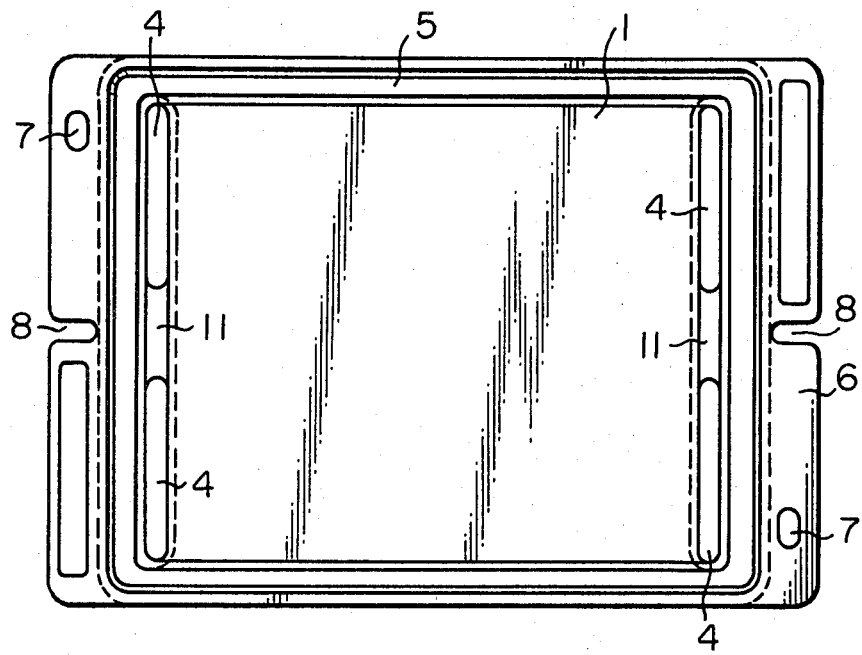
FIG. 1 is a plan view illustrating an embodiment of a supporting body cell according to the present invention.
Figure 2:
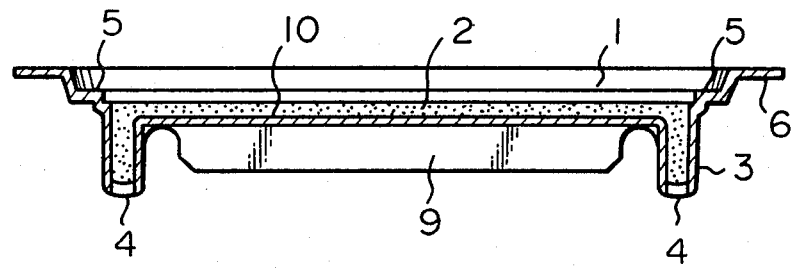
FIG. 2 is a side section of the supporting cell shown in FIG. 1.

Referring to FIGS. 1 and 2, the supporting body cell of the present invention includes a tray 1 having a recessed floor 10, a pair of laterally extending legs 3 each located on the right and left sides of the tray 1, each leg 3 having apertures 4 extending from the lower end thereof and opening into the floor 10 to communicate with the recessed portion of the tray 1, and partitioning members 11 located between adjacent ones of the apertures 4. A gel layer 2 is formed on the floor 10 to a uniform thickness measured from the floor, with the gel filling the apertures 4 in the legs 3 down to the lower end face of the legs. The tray 1 is formed to include a stepped portion 5 surrounding the floor 10 for supporting a cover, not shown, and with a flange-like upper edge 6 at a level higher than that of the stepped portion 5. The upper edge 6 is provided with positioning holes 7 and positioning notches 8. The bottom surface of the floor 10 is provided with longitudinally extending reinforcing ribs or plates 9 which prevent the tray 1 from being distorted by heat generated during electrophoresis.

When used in an apparatus for electrophoresis, the cell having the above construction is supported on the apparatus from below the upper edge 6 or stepped portion 5, and is positioned at a predetermined location by pins or screws passed through the holes 7 and notches 8 provided in the upper edge 6.

As mentioned above, the apertures 4 formed in each leg 3 are partitioned from each other by the partitioning member 11 and therefore do not extend along the width of each leg laterally of the tray 1. In the illustrated embodiment, two apertures are provided in each leg 3, with the partitioning member 11 being disposed at approximately the center of the leg, longitudinally thereof, so that the apertures 4 reside at the outer ends of each leg. The purpose of this arrangement is not only mere reinforcement of the legs, but also a great improvement in operating effects achieved by proper dimensioning of the apertures and partitioning member. More specifically, if electrophoresis were performed using a cell having legs 3 devoid of the centrally located partitioning members 11, namely legs having a continuous, laterally extending aperture, Joule heat generated by the electrophoretic current would tend to dissipate at both sides of the tray 1 owing to cooling by the atmosphere at the leg portions. The result would be an uneven temperature distribution since only the central portion of the tray would attain a high temperature. An uneven temperature distribution has a major influence on the mobility of each component residing in the gel layer. In a fractionated pattern of albumin, for example, mobility toward the high-temperature central portion would be great, giving rise to a pattern curved into a convex form when viewed in plan, so that the results of measurement taken at the central portion and at both sides of the tray would be completely different. This would make it impossible to achieve accurate isolation and quantitative determination of the components.

In accordance with the present invention, the foregoing problem is solved by correcting the current density at the central portion of the tray 1, thereby eliminating any temperature irregularity across the overall area of the gel contained in the tray.

In the illustrated embodiment, we shall assume that the overall thickness of the gel layer inclusive of the leg portions 3 is 2 mm, that the gel layer has a width of 70 mm and a length of 100 mm, and that the electrophoretic current is 20 mA at an ambient temperature of 30° C. Under such conditions, the length of each partitioning member 11 on either side of the central portion of the tray 1, when viewed in plan as in FIG. 1, is set to from 10 to 15 mm. In other words, the area of each partitioning member 11 is set to between 10 and 20% of the cross-sectional area of the corresponding leg portion. Such an arrangement assures that a uniform fractionated pattern free of curves will be obtained over the entire electrophoretic surface.

Figure 3:
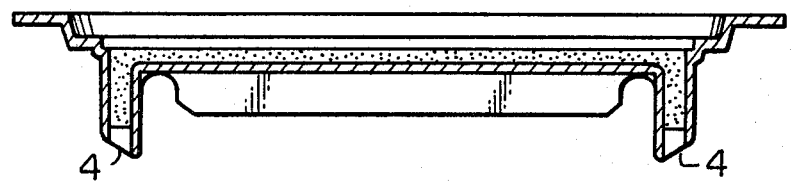
FIG. 3 is side section illustrating a second embodiment of a supporting cell according to the present invention.

It should be noted that too small an area for the apertures 4 and too large a current density per unit area will cause foaming at points where the gel layer 2 contacts the buffer solution. This will result in an uneven current density and make it impossible to obtain a uniform fractionated pattern. To solve this problem, the lower open ends of the legs may be cut at an oblique angle to form inclined apertures 4 when viewed in side section, as shown in the embodiment of FIG. 3, or cut to form wedge-shaped openings 4', as shown in the embodiment of FIG. 4, which is also a side section. Owing to the slanted apertures 4, 4', either arrangement enables bubbles to free themselves from the apertures and rise within the buffer solution so as not to affect the current density. The slanted configuration also increases surface area, so that the density of bubble generation per unit area is reduced.

FIG. 5 illustrates another embodiment of the invention, designed to increase the current density at both sides of the tray 1 in order to uniformalize the temperature of the gel layer 2. As shown, each aperture 4' is shaped into the form of a slender triangle or wedge, meeting apex to apex. Alternatively, a partitioning member 11' of complementary shape may be provided within the leg 3 to afford the same effect.

In another embodiment of the invention, shown in FIG. 6, a layer 12 of metal exhibiting excellent thermal conductivity, such as aluminum, is affixed to the bottom outer surface of the floor 10 by vapor deposition or bonding. This facilitates the spread of heat generated during electrophoresis, thereby preventing uneven temperature distributions. Since the metal layer 12 of aluminum or the like will act as an electrical conductor, it will be necessary to coat the entire surface thereof with an electrically non-conductive substance to prevent current from flowing therethrough.

In either of the arrangements of FIGS. 4 and 5, providing a uniform temperature distribution across the floor 10 of the tray 1 will eliminate disparities in mobility within the gel layer 2 and will form a fractionated pattern which is more faithful to each of the components contained in the sample.

FIG. 7 illustrates how the cell of the present invention may be employed in an actual electrophoretic method. A pair of buffer tanks 15 are prepared, each accommodating an electrode 13 and a buffer solution 14. The tray 1 containing the supporting body, namely the gel layer, is set astride the buffer tanks 13 with the apertures 4 of its leg portions immersed below the liquid level of the buffer solutions. Samples applied to the gel layer are subjected to electrophoresis by energizing the electrodes 13.

Employing the supporting body cell of the present invention as described and illustrated hereinabove makes it possible to avoid non-uniform electrophoresis and a slower rate of electrophoresis caused by foaming. Excellent results can be obtained even when the cell is applied to conventional electrophoretic techniques.

As many apparently widely different embodiments of the present invention may be made without departing from the spirit and scope thereof, it is to be understood that the invention is not limited to the specific embodiments thereof except as defined in the appended claims.

What is claimed is:

1. A cell for a supporting body in an electrophoretic apparatus, which cell comprises a tray having an upper side for accommodating a gel layer serving as the electrophoretic supporting body, a pair of legs, each of said legs extending laterally along an opposing side of said tray, each leg having a plurality of openings communicating between the upper side of the tray and a lower open end of the leg, and partitioning members, each partitioning member being disposed between adjacent ones of said openings to laterally partition the supporting body at the opposing sides.

2. The cell for a supporting body according to claim 1, in which the total area of said partitioning members is 10 to 20% of the total opening area of said openings.

3. The cell for a supporting body according to claim 1 or claim 2, in which the lower open end of each leg is cut off at an oblique angle to form a slanted or wedge-shaped profile.

4. The cell for a supporting body according to claim 1 or claim 2 in which the opening in each leg is tapered toward the center of said tray to form a slender triangular or wedge-shaped profile.

5. The cell for a supporting body according to claim 1, in which a material having excellent thermal conductivity is provided over the bottom surface of said tray.

6. The cell of a supporting body according to claim 1, in which said openings are located adjacent lateral extremities of said tray and said partitioning members are located adjacent the centers of said legs.

7. The cell for a supporting body according to claim 6, in which each of said legs includes first and second openings which are spaced from one another by a centrally located one of said partitioning members.

8. A cell for a supporting body in an electrophoretic apparatus comprising a tray having an upper side for accommodating a gel layer serving as the electrophoretic supporting body, a pair of laterally extending legs, one of said legs being located adjacent each of the longitudinally spaced opposed sides of said tray, each of said legs having a plurality of openings communicating between the upper side of the tray and a lower open end of the leg which is adapted to be immersed into buffer solution, and a plurality of partitioning members, said openings and partitioning members being arranged and constructed so that a major portion of the cross-sectional area of said openings is primarily located adjacent the lateral extremities of said tray and supporting body to provide a uniform temperature distribution and current density across the cell during electrophoresis.

9. A cell for a supporting body according to claim 8, in which each of said legs has an elongated shape and includes first and second openings which are spaced from one another by an associated one of said partitioning members.

10. The cell for a supporting body according to claim 3, in which the opening in each leg is tapered toward the center of said tray to form a slender triangular or wedge-shaped profile.

* * * * *